(12) United States Patent
Fitzgerald et al.

(10) Patent No.: US 8,557,228 B2
(45) Date of Patent: Oct. 15, 2013

(54) AQUEOUS ANTIPERSPIRANT COMPOSITION

(75) Inventors: Michael C. Fitzgerald, Oakhurst, NJ (US); Long Pan, Cherry Hill, NJ (US); Iraklis Pappas, Pennsauken, NJ (US); LaTonya Kilpatrick-Liverman, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/518,957

(22) PCT Filed: Dec. 16, 2010

(86) PCT No.: PCT/US2010/060633
§ 371 (c)(1),
(2), (4) Date: Jun. 25, 2012

(87) PCT Pub. No.: WO2011/087702
PCT Pub. Date: Jul. 21, 2011

(65) Prior Publication Data
US 2012/0308501 A1   Dec. 6, 2012

Related U.S. Application Data

(60) Provisional application No. 61/289,433, filed on Dec. 23, 2009.

(51) Int. Cl.
*A61K 8/41* (2006.01)
*A61K 8/42* (2006.01)
*A61K 8/43* (2006.01)

(52) U.S. Cl.
USPC .......................................................... 424/65

(58) Field of Classification Search
None
See application file for complete search history.

(56) References Cited

U.S. PATENT DOCUMENTS

| 2,230,082 A | 1/1941 | Montenier |
| 3,928,557 A | 12/1975 | Wright et al. |
| 3,932,609 A | 1/1976 | Rosenstreich et al. |
| 3,981,986 A | 9/1976 | Rubino |
| 4,069,299 A | 1/1978 | Hodgson |
| 4,113,852 A | 9/1978 | Kenkare et al. |
| 4,777,034 A | 10/1988 | Olivier et al. |
| 1,125,277 A | 3/1994 | Wallace et al. |
| 5,676,936 A | 10/1997 | Park |
| 6,007,799 A | 12/1999 | Lee et al. |

(Continued)

FOREIGN PATENT DOCUMENTS

| CA | 2257559 | 12/1997 |
| DE | 102005026355 | 12/2006 |

(Continued)

OTHER PUBLICATIONS http://en.wikipedia.org/wiki/Aluminum_oxide, 2012.*

(Continued)

*Primary Examiner* — Carlos Azpuru
(74) *Attorney, Agent, or Firm* — Michael F. Morgan

(57) ABSTRACT

An aqueous antiperspirant/deodorant composition comprising: (a) at least one active chosen from an antiperspirant active and a deodorant active, (b) a mixture comprising at least one basic compound chosen from a basic amide and a basic amine and a counterpart material for the basic amide and/or basic amine, and (c) at least 10 weight % water. Also, a method of manufacturing the composition.

34 Claims, 3 Drawing Sheets

(56) References Cited

U.S. PATENT DOCUMENTS

| | | | |
|---|---|---|---|
| 6,375,937 | B1 | 4/2002 | Chopra et al. |
| 6,960,338 | B2 | 11/2005 | Li et al. |
| 7,074,394 | B2 | 7/2006 | Li et al. |
| 7,105,691 | B2 | 9/2006 | Holerca et al. |
| 7,303,743 | B2 | 12/2007 | Hurley et al. |
| 2003/0044368 | A1 | 3/2003 | Tsuchikura |
| 2004/0077519 | A1 | 4/2004 | Price et al. |
| 2004/0097755 | A1 | 5/2004 | Abbott et al. |
| 2004/0109833 | A1 | 6/2004 | Tang et al. |
| 2004/0198998 | A1 | 10/2004 | Holerca et al. |
| 2006/0094620 | A1 | 5/2006 | Jordan et al. |
| 2006/0094621 | A1 | 5/2006 | Jordan et al. |
| 2006/0204463 | A1 | 9/2006 | Tang et al. |
| 2007/0110687 | A1 | 5/2007 | Mattai et al. |
| 2007/0196308 | A1 | 8/2007 | Popoff et al. |
| 2008/0070966 | A1 | 3/2008 | Elder et al. |
| 2009/0257970 | A1 | 10/2009 | Bloom |

FOREIGN PATENT DOCUMENTS

| | | |
|---|---|---|
| EP | 0281812 | 9/1988 |
| EP | 0914138 | 5/1999 |
| WO | WO 2011-079001 | 6/2001 |
| WO | WO 2006/091417 | 8/2006 |
| WO | WO 2007/059530 | 5/2007 |
| WO | WO 2007/064756 | 6/2007 |
| WO | WO 2011/087701 | 7/2011 |

OTHER PUBLICATIONS

Abbott et al., 2003, "Novel Solvent Properties of Choline Chloride/Urea Mixtures", Chemical Communications 2003(1);70-71.
Abbott et al., 2004 "Deep Eutectic Solvents Formed between Choline Chloride and Carboxylic Acids; Versatile Alternatives to Ionic Liquids", Journal of The American Chemical Society 126:9142-9147.
Binnemans, 2005, "Ionic Liquid Crystals", Chemical Reviews 105:4148-4204.
Binnemans, 2007, "Lanthanides and Actinides in Ionic Liquids", Chemical Reviews 107:2592-2614.
Chi et al., 1998, "Preventing Discoloration of Squalene-soiled Cotton Fabrics with Antioxidants", Journal of Surfactants and Detergents 1(4):523-527.
Coehlo-Sampaio et al., 1994, "Betaine Counteracts Urea-induced Conformational Changes and Uncoupling of the Human Erythrocyte, $Ca^{2+}$ Pump", European Journal of Biochemistry 221:1103-1110.
Davis et al., 2003, "From Curiosities to Commodities: Ionic Liquids Begin the Transition", Chemical Communications 11:1209-1312.
Dupont et al., 2002, "Ionic Liquid (Molten Salt) Phase Organometallic Catalysis", Chem. Rev. 102:3667-3692.
Endres et al., 2006, "Air and Water Stable Ionic Liquids in Physical Chemistry", Physical Chemistry Chemical Physics 8:2101-2116.
FDA, 1978, Monograph on Antiperspirant Dry Products, Oct. 10, 1978.
Feng et al., 2007, "Speciation of Hydroxyl-Al Polymers Formed through Simultaneous Hydrolysis of Aluminum Salts and Urea", Colloids & Surfaces A 303:241-248.
Greaves et al., 2008, "Protic Ionic Liquids: Properties and Applications", Chemical Reviews 108:206-237.
Hardacre et al., 2007, "Structure and Solvation in Ionic Liquids", Accounts of Chemical Research 40:1146-1155.
Holzle et al., 1984, "Structural Changes in Axillary Eccrine Glands Following Long-term Treatment with Aluminium Chloride Hexahydrate Solution", British Journal of Dermatology 110:399-403.
Hu et al., 2005, "Effects of the Structures of Ionic Liquids on Their Physical-Chemical Properties and the Phase Behavior of Mixtures Involving Ionic Liquids".
Huddleston et al., 2001, "Characterization and Comparison of Hydrophilic and Hydrophobic Room Temperature Ionic Liquids Incorporating the Imidazolium Cation", Green Chemistry 3:156-164.
Morrison, et al., 2009, Characterization of Thermal Behavior of Deep Eutectic Solvents and Their Potential as Drug Solubilization Vehicles, International journal of Pharmacy 378:136-139.
Nockemann et al., 2006, "Task-Specific Ionic Liquid for Solubilizing Metal Oxides", Journal of Physical Chemistry B 110:20978-20992.
Padua et al., 2007, "Molecular Solutes in Ionic Liquids: A Structural Perspective", Accounts of Chemical Research 40:1087-1096.
Parnham et al., 2007, "Ionothermal Synthesis of Zeolites, Metal-Organic Frameworks, and Inorganic-Organic Hybrids", Accounts of Chemical Research 40:1005-1013.
Parvulescu et al., 2007, "Catalysis in Ionic Liquids", Chemical Reviews 107:2615-2665.
PCT/US2010/060630—ISR and Written Opinion mailed May 25, 2012.
PCT/US2010/060633—ISR and Written Opinion mailed May 24, 2012.
PCT/US2010/060634—ISR and Written Opinion mailed May 25, 2012.
Plechkova et al., 2008, "Applications of Ionic Liquids in the Chemical Industry", Chemical Society Reviews 37:123-150.
Ranke et al., 2007, "Design of Sustainable Chemical Products—The Example of Ionic Liquids", Chemical Reviews 107:.2183-2206.
Rantwijk et al., 2007, "Biocatalysts in Ionic Liquids", Chemical Reviews 107:2757-2785.
Rogers et al., 2007, "Ionic Liquids", Accounts of Chemical Research 40(11):1077-1078.
RSC, 2005, "Salty Solvents—Ionic Really", Royal Society of Chemicals.
Schaber et al., 2004, "Thermal Decomposition (pyrolysis) of Urea in an Open Reaction Vessel", Thermochimicta Acta 424:131-142.
Shafran et al., 2004, "High Temperature Speciation Studies of A1-Ion Hydrolysis", Advanced Enigineering Materials 6(10):836-839.
Shaw et al., 1955, "The Decomposition of Urea in Aqueous Media", Journal of the American Chemistry Society 77(18):4729-4733.
Short, 2006, "Out of the Ivory Tower: Ionic Liquids Are Starting to Leave Academic Labs and Find Their Way into a Wide Variety of Industrial Applications". Chemical & Engineering: News 84(17):15-21.
Smiglak et al., 2007, "The Second Evolution of Ionic Liquids: From Solvents and Separations to Advanced Materials—Eneregetic Examples from the Ionic Liquid Cookbook", Accounts of Chemical Research 40: 1182-1192.
Vogels et al., 2005, "Honogenious Forced Hydrolysis of Aluminum Through the Thermal Decomposition of Urea", Journal of Colloid and Interface Science 285:86-93.
Wang et al., 2006, "A Theoretical Investigation of the Interactions between Water Molecules and Ionic Liquids", Journal of Physical Chemistry B 110:24646-24651.
Welton, 1999, "Room-Temperature Ionic Liquids. Solvents for Synthesis and Catalysis", Chemical Reviews 99:2071-2083.
Wikipedia entry, 2004, "Ionic Liquid".
Wikipedia entry, 2005, "Deep Eutectic Solvent".
Yancey et al., 1982, "Living with Water Stress: Evolution of Osmolyte Systems", Science 217:1214-1222.

* cited by examiner

AQUEOUS ANTIPERSPIRANT COMPOSITION

CROSS REFERENCE TO RELATED APPLICATIONS

This application is a national stage entry under 35 U.S.C. 371 of International Patent Application No. PCT/US2010/060633, filed 16 Dec. 2010, which claims priority to U.S. Provisional Patent Application No. 61/289,433, filed on 23 Dec. 2009, which is incorporated herein by reference.

BACKGROUND

There have been several forms of antiperspirant products, such as sticks, soft solids, roll-ons, and aerosols. The antiperspirant products may additionally contain deodorant actives. The different forms deliver antiperspirant actives, and optionally deodorant actives, to axillary areas. There can be disadvantages when formulating these types of products.

One disadvantage is that when an antiperspirant active is included, steps need to be taken to stabilize the antiperspirant from hydrolyzing and polymerizing during storage. When an antiperspirant polymerizes into larger species, the efficacy is reduced.

Another disadvantage is that materials used for delivery, such as in the sticks or soft solids, can leave a white residue on the skin. This can be aesthetically unpleasing when seen on skin or when transferred to clothing during wearing.

It would be advantageous to develop a new form of delivery of antiperspirant and/or deodorant actives.

SUMMARY

Provided is an aqueous antiperspirant/deodorant composition comprising: (a) at least one active chosen from an antiperspirant active and a deodorant active, (b) a mixture comprising at least one basic compound chosen from a basic amide and a basic amine and a counterpart material for the basic amide and/or basic amine, and (c) at least 10 weight % water.

Also provided is a method of producing an aqueous antiperspirant composition, the method comprising the steps of (a) providing a composition of at least one active chosen from an antiperspirant active and a deodorant active, a mixture comprising at least one basic compound chosen from a basic amide and a basic amine and a counterpart material for the basic amide and/or basic amine, and at least 10 weight % water; and (b) heating the composition to form a stabilized system of the at least one active, the mixture, and water.

DETAILED DESCRIPTION

Figure 1:
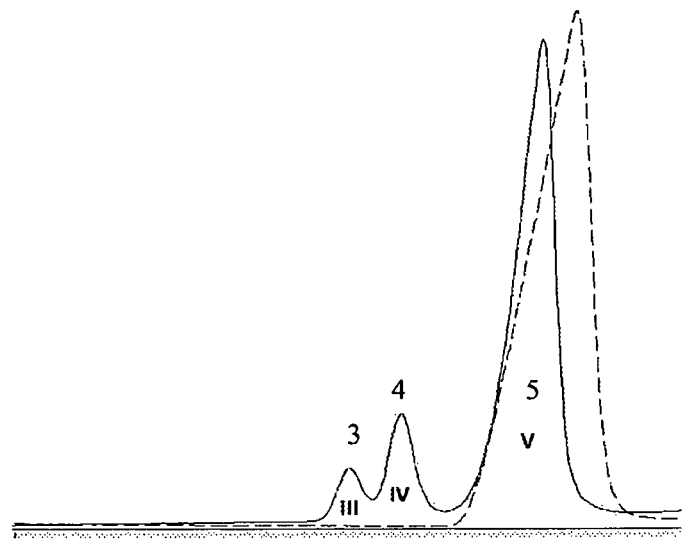
FIG. 1 is an SEC peak distribution of an antiperspirant active produced in accordance with an embodiment of the present invention (solid line) and of a first comparative antiperspirant active (dashed line) not in accordance with to the present invention.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material unless otherwise specified.

Provided is an aqueous antiperspirant/deodorant composition comprising: (a) at least one active chosen from an antiperspirant active and a deodorant active, (b) a mixture comprising at least one basic compound chosen from a basic amide and a basic amine and a counterpart material for the basic amide and/or basic amine, and (c) at least 10 weight % water.

The composition can contain at least 10, 15, 20, 25, or 30 weight % water. In one embodiment, the antiperspirant composition comprises at least 20 weight % water.

The at least one basic compound chosen from a basic amide and a basic amine and the counterpart material are present in the composition as a mixture that can be considered an osmolyte system and/or an ionic liquid. This means that the selection of the type and amount of each material is such that an osmolyte system and/or ionic liquid is formed. This is distinguished from previous compositions in which either of these materials could have been present in an antiperspirant/deodorant composition but not in the form of an osmolyte system and/or ionic liquid. In certain embodiments the amount of the osmolyte system and/or ionic liquid is present in an amount that is 100 weight % minus the amount of water in the composition.

The counterpart material is any material that can form an osmolyte system and/or ionic liquid with the at least one basic compound chosen from a basic amide and a basic amine.

Optionally, the at least one antiperspirant active, the at least one basic compound and the counterpart material form a ternary antiperspirant system.

Optionally, the at least one basic compound is a hydrogen bond donor and/or selected from at least one of urea, arginine, lysine, acetamide, and guanidine. Optionally, the counterpart material is a proton-accepting zwitterionic stabilizing ligand. The counterpart material may comprise at least one of trimethylglycine, trimethylglycine hydrochloride, trimethylamine N-oxide (TMAO), carnitine, sarcosine, opines, taurine, choline, and dimethylsulfoniopropionate.

In one embodiment, the at least one basic compound is urea and the counterpart material is trimethylglycine. The urea and trimethylglycine may be in a molar ratio of 1:0.01 to 1:10, optionally 10:1 to 1:1, optionally about 2:1.

In one embodiment, the at least one basic compound is urea and the counterpart material is trimethylglycine, and the urea and trimethylglycine form a ternary system with the antiperspirant active.

Optionally, the antiperspirant active is present in an amount of 5 to 25 weight %. Optionally, the antiperspirant active comprises an aluminum salt, typically $AlCl_3 \cdot 6H_2O$.

In one embodiment, the at least one basic compound chosen from a basic amide and a basic amine is present in the composition in an amount up to 45 weight %. In other embodiments, the amount is up to 40, 35, 30, 25, 20, 15, or 10 weight %. In other embodiments, the amount is at least 1, 2, 3, 4, or 5 up to any of the previously listed maximum weight %. In one embodiment, the amount is 5 to 10 weight %.

In one embodiment, the counterpart material is present in the composition in an amount up to 45 weight %. In other embodiments, the amount is up to 40, 35, 30, 25, 20, 15, or 10 weight %. In other embodiments, the amount is at least 1, 2, 3, 4, or 5 up to any of the previously listed maximum weight %. In one embodiment, the amount is 5 to 10 weight %.

In one embodiment, the ternary system comprises $AlCl_3 \cdot 6H_2O$ as the antiperspirant active, urea and trimethylglycine. Optionally, the ternary system comprises 5 to 15 weight % $AlCl_3 \cdot 6H_2O$, 5 to 10 weight % urea, and 5 to 10 weight % trimethylglycine.

In certain embodiments, the antiperspirant composition typically has a pH of 2.5 to 6, optionally 3 to 5.

Also provided is a method of producing an aqueous antiperspirant composition, the method comprising the steps of: (a) providing a composition of at least one antiperspirant active including a metal salt, a mixture in which the at least one antiperspirant active is dissolved, and at least 10 weight % water, wherein the mixture comprises at least one basic compound chosen from a basic amide and a basic amine and a counterpart material for the basic amide and/or basic amine, and (b) heating the composition to form a stabilized system of the at least one antiperspirant active, the mixture, and water.

Typically, in step (b) the composition is heated at a temperature of 90 to 110° C. for a period of 1 to 8 hours.

Betaine in IUPAC nomenclature is 1-carboxy-N,N,N-trimethylmethanaminium hydroxide-inner salt, with alternative names including carboxymethyl-trimethyl-ammonium betaine or (carboxymethyl)trimethylammonium hydroxide-inner salt or glycine betaine or glycol betaine or glycyl betaine or trimethylglycine or trimethylglycol. Betaine is not to be confused with betaine surfactants.

The present inventors discovered that antiperspirant compositions containing a metal salt, in particular an aluminum salt, and more particularly $AlCl_3 \cdot 6H_2O$ as the active, can be present as a stabilized solution at a higher pH, and so at a pH closer to that of skin pH, than previous generation antiperspirant compositions containing $AlCl_3 \cdot 6H_2O$ as the active. In particular, the present inventors have found a buffer system that can stabilize an excess of the small aluminum species in those solutions of $AlCl_3 \cdot 6H_2O$ at a pH closer to that of skin, which can provide desired mildness to skin and fabric.

The present inventors have devised a buffer system that can stabilize an excess of the small aluminum species in those solutions at a pH closer to skin pH. This provides an effective route to enhanced sweat protection because the technology is based on a time-tested antiperspirant active, $AlCl_3 \cdot 6H_2O$, and the present inventors have improved upon known low pH effects of that active by raising the pH with a skin-compatible buffer.

Furthermore, the present inventors discovered that hydrothermally treating a combination of an aqueous solution of an antiperspirant active, in particular an aluminum-containing antiperspirant active such as $AlCl_3 \cdot 6H_2O$, in the presence of an organic basic amine and/or amide (e.g. urea) with the addition of a counterpart material (e.g. trimethylglycine) aids the synthesis and improves the characteristics of an antiperspirant composition having the combination of high antiperspirant efficacy and mildness to the skin and clothing. It is believed that under the hydrothermal reaction conditions, urea provides a source of base in situ that gradually raises the pH of the solution to a level dependant on the reaction conditions.

It is known to add buffers, especially urea, to $AlCl_3 \cdot 6H_2O$ solutions to increase the pH. However, it is not known to use a combination of a base such as a urea and a counterpart material. It is also not known that such a combination of components in a ternary system, or the use of a hydrothermal treatment to produce such an antiperspirant active form such a combination of components, can provide enhanced antiperspirant efficacy.

Employed in an aqueous system is a counterpart material, such as trimethylglycine, which aids in synthesis, stabilizes the product, and functions with urea, particularly when a 1:2 trimethylglycine to urea molar ratio is employed, as a complementary stabilizing system.

This permits the ternary antiperspirant system to be synthesized in one step and in one vessel. Such a simple synthesis can select between a multitude of reaction conditions that can be selected for specific outcomes, such as different pH, concentration, etc.

In one embodiment, the ternary antiperspirant system is based on a metal salt, a basic amide/amine, and a counterpart material, preferably a proton-accepting zwitterionic ligand, the latter typically being trimethylglycine, which is a permanent zwitterion.

In one embodiment, the antiperspirant active can provide a number of technical benefits and advantages over known antiperspirant actives and systems.

In particular, the antiperspirant active may provide enhanced efficacy, so that extended protection can be achieved by stabilizing smaller aluminum species, which are known to be more effective antiperspirants, in aqueous solution. The antiperspirant active may provide reduced irritation and fabric damage by raising the pH of the aqueous solution. Such reduced irritation may be achieved by using a skin-compatible buffering system, e.g. urea-trimethylglycine, for the active aluminum compound. Still further, reduced visibility of residue on skin and fabric can be achieved by stabilizing the active in an aqueous solution rather than dispersing an opaque powder in a given formulation or by using an opaque formula base, for example a roll-on formulation.

When urea is used to neutralize aluminum chloride, and the counterpart material provides a stabilizing effect as a ligand, an aqueous liquid state antiperspirant composition is obtained that is mainly composed of the smaller aluminum species, which can be demonstrated by standard Size Exclusion Chromatograph (SEC). The SEC spectrum of this antiperspirant composition is dominated by "peak 5", which is the smaller aluminum species that are known to have very good antiperspirant efficacy.

In certain variations of the carrier comprising the trimethylglycine and urea embodiment, a portion of the urea can be replaced by other buffers or hydrogen bond donors. In one embodiment, 20-50 molar % of the urea can be replaced.

Antiperspirant actives include, but are not limited to, aluminum chloride, in particular $AlCl_3 \cdot 6H_2O$ as the antiperspirant active, aluminum chlorohydrate, aluminum sesquichlorohydrate, aluminum-zirconium hydroxychlorides, complexes or adducts of the above-mentioned active ingredients with glycol, such as propylene glycol (for example, "Rehydrol" II from SummitReheis), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients, listed in the Food and Drug Administration's Monograph on Antiperspirant Drug Products for overall-the-counter human use (Oct. 10, 1973) can be used. Specific examples of commercialized aluminum-zirconium salts include AZP-908 and Z-576 from SummitReheis (Huguenot, N.Y.).

In other embodiments, the antiperspirant active is an aluminum salt and/or an aluminum-zirconium salt, such as those described above, that are further stabilized by betaine and a calcium salt. More information about betaine and calcium salt stabilized antiperspirant salts can be found in U.S. Patent Application Publication No. 2006/0204463 to Tang et al.

In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al.

In other embodiments, the type of salt of interest, an aluminum zirconium tetrasalt or octasalt free of glycine are used wherein aluminum zirconium salt is stabilized by betaine and has a metal to chloride ratio of about 0.9:1 to about 1.3:1 (and in other embodiments of about 0.9:1 to about 1.2:1 or about 0.9:1 to about 1.1:1). For the tetrasalt, the Al/Zr atomic ratio can be about 3.2:1 to about 4.1:1.0 and the betaine:zirconium mole ratio can be about 0.2:1 to about 3.0:1 (or in other embodiments of about 0.4:1 to about 1.5:1). Another salt that can be used is an aluminum chloride salt buffered by betaine, wherein the salt has a metal to chloride ratio of 0.9:1 to 1.3:1 (and in other embodiments of about 0.9:1 to about 1.2:1 or about 0.9:1 to about 1.1:1). For the octasalt the Al/Zr atomic ratio is about 6.2:1 to about 10.0:1 and the betaine:Zr mole ratio is about 0.2:1 to about 3.0:1 (or in other embodiments of about 0.4:1 to about 1.5:1). In one embodiment, in the case of a salt that contains zirconium, the betaine is incorporated during the synthesis of the salt so as to maximize the stabilizing effect this ingredient has (especially on the zirconium species). Alternatively, it can be post added to a glycine-free salt along with additional active phase ingredients to form a betaine stabilized active.

Examples of commercially available glycine-free low M:Cl ratio tetrasalts and octasalts include, but are not limited to, REZAL™ AZP 955 CPG and REZAL™ AZP 885 respectively (both from SummitReheis Chemical Company, Huguenot, N.Y.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

Additionally, the antiperspirant active can be a calcium salt stabilized antiperspirant active. Examples of calcium salt stabilized antiperspirant actives can be found in U.S. Patent Application Publication No. 2006/0204463.

In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active. Antiperspirant actives can include, but are not limited to, the following: astringent salt of aluminum, astringent salt of zirconium, aluminum bromohydrate, aluminum chlorohydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorhydrate. In another embodiment, the antiperspirant active is aluminum zirconium tetrachlorhydrex propylene glycol.

The amount of antiperspirant active can be any of the regulatory allowed amounts for each type of antiperspirant active. In certain embodiments, the amount is up to 25 weight % for an over the counter composition. In certain embodiments, the amount is 5 to 25 weight % of the composition. In other embodiments, the amount is at least 5, 10, or 15 up to 20 weight % of the composition.

Aluminum chloride refers to the hydrate forms. In one embodiment, the hydrate form comprises $AlCl_3.6H_2O$. In one embodiment, the amount of aluminum chloride is up to 20 weight %. In other embodiments, the amount is up to 18, 17, 16, 15, 14, 13, 12, 11, 10, 9, 8, 7, 6, or 5 weight %.

In one embodiment, a ternary system based on (i) an aluminum source; (ii) a basic amine and/or a basic amide; and (iii) a counterpart material, typically a proton-accepting zwitterionic stabilizing ligand, for example trimethylglycine.

The aluminum source may comprise $AlCl_3.6H_2O$ or alternative aluminum sources, such as ACH, ASCH, etc. When the aluminum source is other than $AlCl_3.6H_2O$ it may be necessary to add a pH modifier to control pH to be within the desired mild pH range, for example by adding an acid, such as an inorganic acid, e.g., HCl, or an organic acid.

Non-limiting examples of such basic amine and/or basic amide are urea, arginine, lysine, acetamide, and guanidine.

The counterpart material may comprise trimethylglycine, or alternative or related compounds such as, to give some non-limiting examples, trimethylamine N-oxide (TMAO), carnitine, sarcosine, opines, taurine, choline, dimethylsulfoniopropionate, etc.

One embodiment provides a ternary system based on (i) $AlCl_3.6H_2O$ as an aluminum source; (ii) urea and (iii) trimethylglycine, to provide an $AlCl_3.6H_2O$-urea-trimethylglycine ternary system.

For the ternary system of the antiperspirant active according to an embodiment employs $AlCl_3.6H_2O$ as the aluminum source, such as in the $AlCl_3.6H_2O$-urea-trimethylglycine ternary system, the final $AlCl_3.6H_2O$ concentration can be any amount, but it is usually ≤15 weight %, to comply with an FDA Monograph regulation.

The synthesis of an antiperspirant active composition, as a ternary system, according to various embodiments may be carried out using a hydrothermal treatment as follows. In particular, an aqueous solution of the (i) aluminum source, for example $AlCl_3.6H_2O$; (ii) at least one basic compound chosen from a basic amide and a basic amine, for example urea; and (iii) a counterpart material, for example trimethylglycine, that contains at least 10 (preferably at least 20) weight % water is prepared. In certain embodiments, the amounts of components (i), (ii) and (iii) are selected so that all of the components will fall within the proper concentration ranges and ratios when diluted and/or formulated to a desired product formula. The initial synthesized ternary system and the subsequent dilution and/or formulation are selected to permit the final composition to have a portion of its composition which can be comprised of additional formulators, such as water, silicones, emulsifiers, etc., which can be added after synthesis of the ternary antiperspirant active system.

The aqueous solution is heated at an elevated temperature, typically 90° C. to 110° C., for example 100° C., preferably with constant stirring. The heating is conducted for a selected period of time, typically 1 to 8 hours, for example 3 hours, depending on concentrations in the synthesis mixture and the desired final pH.

After heating the resulting solution can be stored for some amount of time or immediately diluted or formulated.

The pH of the antiperspirant active ternary system is typically within the range of greater than pH 2.5 and up to pH 6. This provides the property of mildness to skin. In certain embodiments, the pH is 3 to 5, 3.5-4.5, or 3.5-4. Typically, when the $AlCl_3.6H_2O$ content is at 12 weight % in the final antiperspirant composition to provide enhanced antiperspirant efficacy the pH is 3.5 to 4 to provide mildness to skin and fabric.

The aluminum species size is determined using size exclusion chromatography (SEC) which is well known for use in antiperspirant active analysis. The SEC results for when $AlCl_3.6H_2O$ is used in certain embodiments indicate that the peak 5 area is ≥50%, or ≥75%, of the total peak area, and that the combined area of peaks 4 and 5 is ≥60%, or ≥80%, of the total peak area. Also the combined area of peaks 3 and 4 in certain embodiments is <50%, or <30% of the total peak area. Using $^{27}Al$ NMR, qualitative analysis shows an abundance of Al monomer, and may also indicate the presence of small Al polymers such as Al dimer, $Al_{13}$ and $Al_{30}$.

The SEC data is obtained using an SEC chromatogram using the following parameters: Waters® 600 analytical pump and controller, Rheodyne® 7725I injector, Protein-Pak® 125 (Waters) column, Waters 2414 Refractive Index Detector. 5.56 mM nitric acid mobile phase, 0.50 ml/min flow rate, 2.0 microliter injection volume. Data was analyzed using Water® Empower software (Waters Corporation, Milford, Mass.). The concentration of the antiperspirant in aqueous solution does not affect the retention time in the machine. The relative retention time ("Kd") for each of these peaks varies depending on the experimental conditions, but the peaks remain relative to each other.

Examples of deodorant actives include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyl-trimethylammomium bromide, cetyl pyridinium chloride, farnesol (3,7,11-trimethyl-2,6,10-dodecatrien-1-ol), bactericides, and/or bacteriostats. In certain embodiments, the amount of deodorant actives is 1 to 20 weight % of the composition.

A stabilizing agent can optionally be included in the composition. The stabilizing agent is any material that is present in an amount such that the composition is liquid below 100° C. The amount of stabilizing agent varies by the stabilizing capability of each stabilizing agent. In certain embodiments, the amount of stabilizing agent is 1 to 20 weight % of the composition. In other embodiments, the amount of stabilizing agent is at least 1, 2, 3, 4, 5, 6, 7, 8, 9, or 10 up to 20 weight % of the composition. In other embodiments, the amount is less than 20, 15, 10, 9, 8, 7, 6, 5, 4, 3, or 2 down to 1 weight % of the composition. Examples of stabilizing agents include, but are not limited to, PPG-14 butyl ether, chloride salts, sodium chloride (NaCl), potassium chloride, bromides, nitrates, organic acids, glycerin, alcohol, ethanol, and isopropanol.

To improve the skin feel of the composition, skin-feel additives can be added. In one embodiment, the amount of skin-feel additives is 1 to 8 weight % of the composition. In other embodiments, the amount is at least 1, 2, 3, 4, or 5 up to 8 weight %. In other embodiments, the amount is less than 8, 7, 6, 5, 4, 3, or 2 down to 1 weight %. In certain embodiments, the amount of skin-feel additives is up to 10 weight % to allow for more delivery of the antiperspirant active.

The optional skin-feel additives that can be used include, but are not limited to, water, isopropanol, ethanol, cocamidopropyl betaine, cyclomethicone (such as DC345), PEG-12 dimethicone copolyol (DC5329), steareth-2/steareth-20, polyoxyethylene homopolymer (POLYOX™ WSR-N 750 from Dow Chemical), palm kernel oil, mineral oil, and silicone polyether wax (Silwax from Siltech).

The antiperspirant/deodorant composition may be present in any convenient form, such as a water-based roll-on, or it can be formulated into a stick, soft solid, gel, or aerosol. The antiperspirant actives may be dissolved in aqueous solution in these compositions, which may accordingly be transparent compositions. This can substantially avoid having white residue when applied to skin, which is undesirable to consumers. The antiperspirant/deodorant composition provides a transparent product with no white residue. Also, the product may have a long shelf life, for example up to 10 years can be expected.

The composition can optionally contain emollients in any desired amount to achieve a desired emollient effect. Emollients are known in the art and are used to impart a soothing effect on the skin. Non-volatile emollients are preferable. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material is phenyl trimethicone. Non-limiting examples of emollients can be found in U.S. Pat. No. 6,007,799. Examples include, but are not limited to, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl)succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide.

The composition can contain a fragrance. Any known fragrance can be used in any desired amount. In one embodiment, the amount of fragrance is 0.01 to 10 weight %.

Antioxidants may be added to the composition, preferably to act as ingredient protectants and for maintenance of long-term stability of the composition. Examples of antioxidants include, but are not limited to butylated hydroxytoluene, pentaerythrityl tetra-di-t-butyl hydroxyhydrocinnamate (Tinogard™ TT from Ciba).

Any of the liquid antiperspirant/deodorant compositions can be applied to axillary areas to reduce sweat and/or odor. The compositions can be applied by hand or via their packaging.

SPECIFIC EMBODIMENTS

The invention is further described in the following examples. The examples are merely illustrative and do not in any way limit the scope of the invention as described and claimed.

Example 1

This Example synthesized an antiperspirant active composition using a solution containing 30 weight % water, 26.45 weight % $AlCl_3.6H_2O$, 22.05 weight % urea, and 21.5 weight % trimethylglycine. This solution was diluted with diluents or formulated to provide a final target concentration (after dilution or formulation) of 12 weight % $AlCl_3.6H_2O$, 10 weight % urea and 9.75 weight % trimethylglycine (and 13.6 weight % water from the original 30 weight % water present in the synthesized solution). The synthesized solution therefore provided for, in addition to the water in the synthesized solution, up 54.6 weight % chosen diluent(s)/formulation additives to be formulated together with the antiperspirant active composition.

During the synthesis process, the solution containing 30 weight % water, 26.45 weight % $AlCl_3.6H_2O$, 22.05 weight % urea, and 21.5 weight % trimethylglycine was heated at 100° C. for 3 hours with constant stirring. Any mass loss during heating (due to evaporation of water and/or off-gassing of $CO_2$) was compensated with water directly after synthesis. After heating, the solution was diluted with water to reach the target concentration for the resultant antiperspirant active of 12% $AlCl_3.6H_2O$, 10% urea, and 9.75% trimethylglycine.

The pH of the resultant diluted solution was measured and found to be is stable at pH 4.05.

The resultant diluted solution containing the resultant antiperspirant active was analyzed using SEC and $^{27}Al$ NMR.

For the SEC analysis, FIG. 1 illustrates an SEC chromatogram of the resultant antiperspirant active (the solid line). Later elution times indicate smaller particle size, corresponding to enhanced antiperspirant efficacy. It may be seen that there is a large peak 5, a much smaller peak 4, and a smaller still peak 3.

The ternary antiperspirant active system according to different embodiments may be compared to known compositions.

One such known composition is CertainDri®, a commercially available over-the-counter antiperspirant based on a 12 weight % solution of $AlCl_3.6H_2O$ buffered with $NaHCO_3$ to pH ~2.5. That composition has been analyzed using SEC, the SEC profile containing peak 5 only.

Other such known composition comprise $Al_{13}$ and $Al_{30}$ polymer compositions which can be synthesized at high purity in the laboratory and elute entirely under peak 4 when analyzed with that SEC method. A currently employed ACH that returns SEC peaks 3, 4, and 5, and $^{27}Al$ NMR analysis of the antiperspirant system validates an abundance of Al monomers, and may also indicate the presence of small Al polymers (e.g., Al dimer), $Al_{13}$, and $Al_{30}$.

For comparison, FIG. 1 also illustrates an SEC chromatogram of the commercially available CertainDri® antiperspirant active (the dashed line).

The Certain-Dri antiperspirant active has only one peak at the latest elution time. However, the composition has very low pH and is not mild. In contrast, the resultant antiperspirant active has higher pH (4.05 in this Example) and is mild. The peak 5 has been substantially stabilized, compared to the high efficacy Certain-Dri antiperspirant active, at a higher pH, while preventing significant formation of species as large or larger than peak 4. It is evident in the chromatogram that the resultant antiperspirant active has maintained predominantly small species, as represented by the peak 5 area comprising about 80% of the total area Peak 5).

Figure 2:
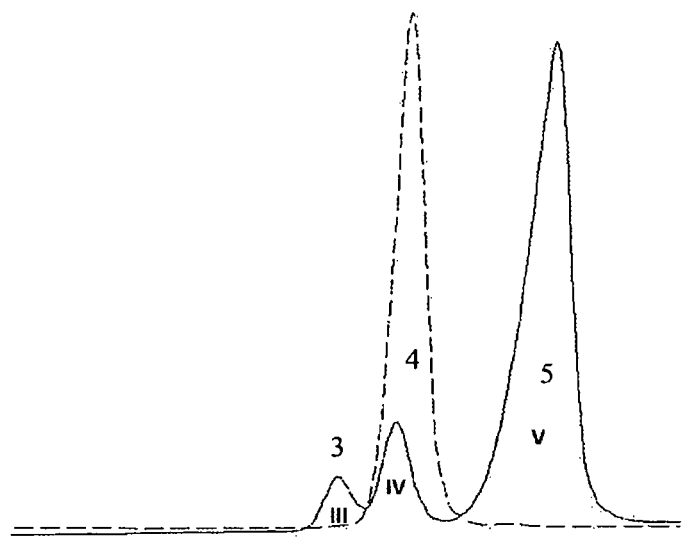
FIG. 2 is an SEC peak distribution of an antiperspirant active produced in accordance with an embodiment of the present invention (solid line) and of a second comparative antiperspirant active (dashed line) not in accordance with to the present invention.

Additionally for the SEC analysis, FIG. 2 compares the SEC chromatogram of the resultant antiperspirant active (the solid line) against the SEC chromatogram of the known $Al_{13\text{-}mer}$ and $Al_{30\text{-}mer}$ salts (the dashed line). It is evident from the chromatograms that the $Al_{13\text{-}mer}$ and $Al_{30\text{-}mer}$ salts have reduced efficacy as compared to the resultant antiperspirant active because of the predominance of the peak 4 area for the $Al_{13\text{-}mer}$ and $Al_{30\text{-}mer}$ salts as compared to the predominance of the peak 5 area the resultant antiperspirant active.

Figure 3:
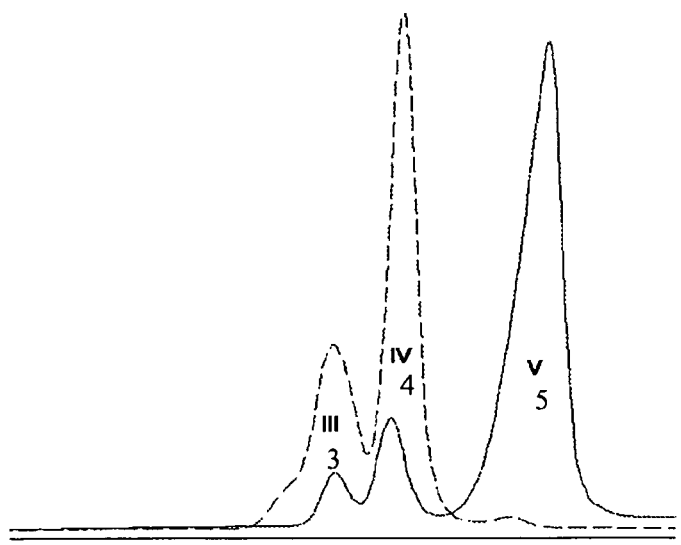
FIG. 3 is an SEC peak distribution of an antiperspirant active produced in accordance with an embodiment of the present invention (solid line) and of a third comparative antiperspirant active (dashed line) not in accordance with to the present invention.

Yet further for the SEC analysis, FIG. 3 compares the SEC chromatogram of the resultant antiperspirant active (the solid line) against the SEC chromatogram of the current commercially available ACH salt (the dashed line). Compared to ACH, the resultant antiperspirant active has reduced peaks 3 and 4, and increased peak 5 representing stabilized smaller species, at a similar pH. The minimized peak 3 and 4 species compared to ACH represents enhanced antiperspirant efficacy.

Figure 4:
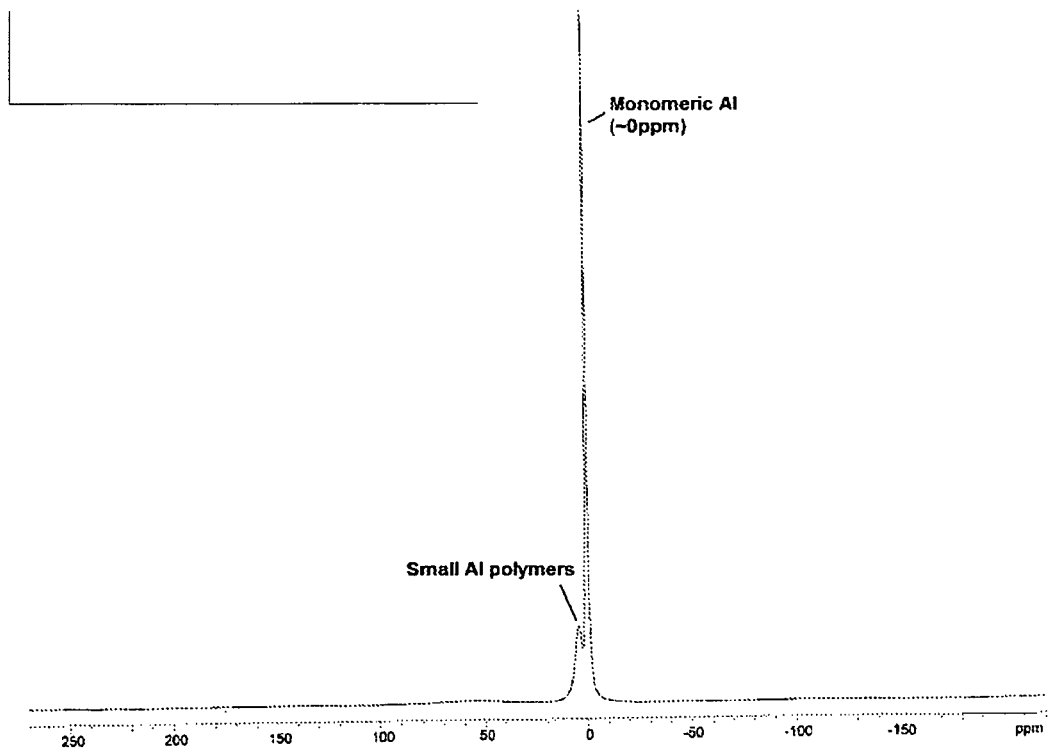
FIGS. 4 and 5 show $^{27}$Al NMR spectra of an antiperspirant active produced in accordance with an embodiment of the present invention respectively before and after hydrothermal treatment of the antiperspirant active.
Figure 5:
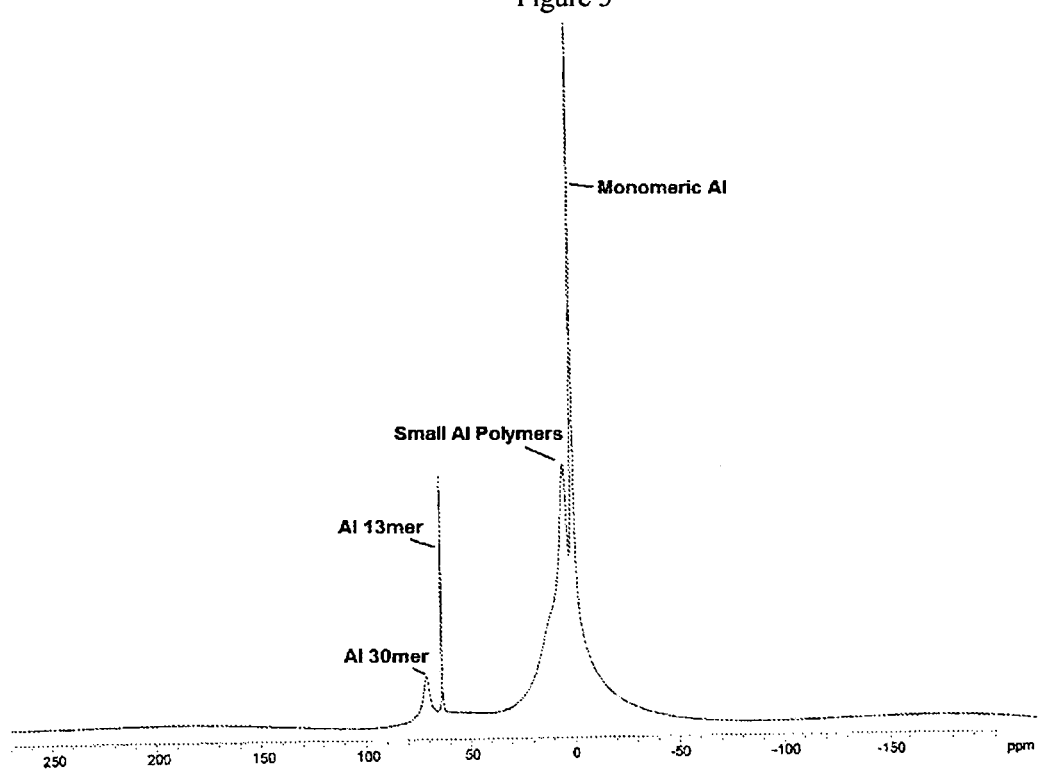

FIGS. 4 and 5 show $^{27}Al$ NMR results for the resultant antiperspirant active respectively before and after hydrothermal treatment of the ternary system.

In FIG. 4, before hydrothermal treatment in the $^{27}Al$ NMR result there is a strong resonance at ~0 ppm corresponding to monomeric Al, and a small peak at ~4-10 ppm corresponding to small Al polymers. After hydrothermal synthesis, the $^{27}Al$ NMR result of FIG. 5 indicates that Al monomer is still present, there is a significant boost in small Al polymers, and two new peaks at ~63 ppm and ~70 ppm appear corresponding to formation of $Al_{13}$ and $Al_{30}$ respectively.

What is claimed is:

1. An aqueous antiperspirant composition comprising:
   a. an antiperspirant active,
   b. a mixture comprising at least one basic compound chosen from a basic amide and a basic amine and a counterpart material for the basic amide and/or basic amine, and
   c. at least 10 weight % water,
   wherein the antiperspirant active, the at least one basic compound chosen from a basic amide and a basic amine, and the counterpart material are present such that a selection of a type of each and an amount of each is such that an osmolyte system and/or ionic liquid is formed.

2. The antiperspirant composition of claim 1, wherein the at least one basic compound chosen from a basic amide and a basic amine is present in an amount up to 45 weight %.

3. The antiperspirant composition of claim 1, wherein the counterpart material is present in an amount up to 45 weight %.

4. The antiperspirant composition of claim 1, wherein the at least one basic compound is chosen from at least one of urea, arginine, lysine, acetamide, and guanidine.

5. The antiperspirant composition of claim 1, wherein the counterpart material is a proton-accepting zwitterionic stabilizing ligand for the antiperspirant active.

6. The antiperspirant composition of claim 1, wherein the counterpart material is at least one material chosen from trimethylglycine, trimethylglycine hydrochloride, trimethylamine N-oxide (TMAO), carnitine, sarcosine, opines, taurine, choline, and dimethylsulfoniopropionate.

7. The antiperspirant/deodorant composition of claim 1, wherein the at least one basic compound is urea and the counterpart material is trimethylglycine.

8. The antiperspirant composition of claim 7, wherein the urea and trimethylglycine are in a molar ratio of 1:0.01 to 1:10.

9. The antiperspirant composition of claim 7, wherein the urea and trimethylglycine are in a molar ratio of about 2:1.

10. The antiperspirant composition of claim 1, wherein the antiperspirant active is present in an amount of 5 to 25 weight %.

11. The antiperspirant composition of claim 1, wherein the antiperspirant active comprises an aluminum salt.

12. The antiperspirant composition of claim 11, wherein the antiperspirant active comprises $AlC_3.6H_2O$.

13. The antiperspirant composition of claim 12, wherein the ternary system comprises $AlCl_3.6H_2O$ as the antiperspirant active, urea and trimethylglycine.

14. The antiperspirant composition of claim 13, wherein the ternary system comprises 5 to 15 weight % $AlCl_3.6H_2O$, 5 to 10 weight % urea, and 5 to 10 weight % trimethylglycine.

15. The antiperspirant composition of claim 1, which has a pH of 2.5 to 6.

16. The antiperspirant/deader-ant composition of claim 1, comprising at least 20 weight % water.

17. A method of producing an aqueous antiperspirant composition, the method comprising the steps of:
   a. providing an antiperspirant active, a mixture comprising at least one basic compound chosen from a basic amide and a basic amine and a counterpart material for the basic amide and/or basic amine, and at least 10 weight % water, wherein the antiperspirant active, the at least one basic compound chosen from a basic amide and a basic amine, and the counterpart material are present such that a selection of a type of each and an amount of each is such that an osmolyte system and/or ionic liquid can be formed; and
   b. heating the composition to form a stabilized system in a form of the osmolyte system and/or ionic liquid.

18. The method of claim 17, wherein the at least one basic compound chosen from a basic amide and a basic amine is present in an amount up to 45 weight %.

19. The method of claim 17, wherein the counterpart material is present in an amount up to 45 weight %.

20. The method of claim 17, wherein the mixture comprises at least 20 weight % water.

21. The method of claim 17, wherein the at least one basic compound is chosen from at least one of urea, arginine, lysine, acetamide, and guanidine.

22. The method of claim 17, wherein the counterpart material is a proton-accepting zwitterionic stabilizing ligand for the antiperspirant active.

23. The method of claim 17, wherein the counterpart material is at least one material chosen from trimethylglycine, trimethylglycine hydrochloride, trimethylamine N-oxide (TMAO), carnitine, sarcosine, opines, taurine, choline, and dimethylsulfoniopropionate.

24. The method of claim 17, wherein the at least one basic compound is urea and the counterpart material is trimethylglycine.

25. The method of claim 24, wherein the urea and trimethylglycine are in a molar ratio of 1:0.01 to 1:10.

26. The method of claim 24, wherein the urea and trimethylglycine are in a molar ratio of about 2:1.

27. The method of claim 17, wherein the antiperspirant active is present in an amount of 5 to 25 weight %.

28. The method of claim 17, wherein the antiperspirant active comprises an aluminum salt.

29. The method of claim 28, wherein the antiperspirant active comprises $AlCl_3.6H_2O$.

30. The method of claim 29, wherein the ternary system comprises $AlCl_3.6H_2O$ as the antiperspirant active, urea and trimethylglycine.

31. The method of claim 30, wherein the ternary system comprises 5 to 15 weight % $AlCl_3.6H_2O$, 5 to 10 weight % urea, and 5 to 10 weight % trimethylglycine.

32. The method of claim 17, wherein the aqueous antiperspirant composition has a pH of 2.5 to 6.

33. The method of claim 17, wherein in step (b) the mixture is heated at a temperature of 90 to 110° C. for a period of 1 to 8 hours.

34. A method comprising applying to an axillary area the aqueous antiperspirant composition of claim 1.

* * * * *